US010925822B2

(12) United States Patent
Djedour

(10) Patent No.: US 10,925,822 B2
(45) Date of Patent: Feb. 23, 2021

(54) PROCESS FOR PREPARING A DERMATOLOGICAL COMPOSITION COMPRISING OLEOSOMES

(71) Applicant: GALDERMA RESEARCH & DEVELOPMENT, Biot (FR)

(72) Inventor: Amel Safia Djedour, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/404,933

(22) PCT Filed: May 30, 2013

(86) PCT No.: PCT/EP2013/061192
§ 371 (c)(1),
(2) Date: Dec. 1, 2014

(87) PCT Pub. No.: WO2013/178752
PCT Pub. Date: Dec. 5, 2013

(65) Prior Publication Data
US 2015/0190327 A1    Jul. 9, 2015

Related U.S. Application Data

(60) Provisional application No. 61/654,680, filed on Jun. 1, 2012.

(30) Foreign Application Priority Data

Jun. 1, 2012    (FR) ...................................... 1255107

(51) Int. Cl.
| | | |
|---|---|---|
| *A61K 8/49* | (2006.01) | |
| *A61K 8/36* | (2006.01) | |
| *A61K 8/39* | (2006.01) | |
| *A61K 8/06* | (2006.01) | |
| *A61K 9/107* | (2006.01) | |
| *A61K 9/00* | (2006.01) | |
| *A61K 47/14* | (2017.01) | |
| *A61K 8/81* | (2006.01) | |
| *A61K 8/37* | (2006.01) | |
| *A61Q 19/00* | (2006.01) | |
| *A61K 9/127* | (2006.01) | |

(52) U.S. Cl.
CPC ............ *A61K 8/4913* (2013.01); *A61K 8/062* (2013.01); *A61K 8/361* (2013.01); *A61K 8/37* (2013.01); *A61K 8/375* (2013.01); *A61K 8/39* (2013.01); *A61K 8/81* (2013.01); *A61K 9/0014* (2013.01); *A61K 9/107* (2013.01); *A61K 9/127* (2013.01); *A61K 47/14* (2013.01); *A61Q 19/00* (2013.01); *A61K 2800/10* (2013.01); *A61K 2800/805* (2013.01)

(58) Field of Classification Search
CPC .... A61K 8/4913; A61K 9/107; A61K 9/0014; A61K 47/14; A61K 8/81; A61K 8/375; A61K 9/127; A61K 8/37; A61K 8/361; A61K 8/39; A61K 8/062; A61K 2800/805; A61K 2800/10; A61Q 19/00; A61P 17/00
See application file for complete search history.

(56) References Cited

U.S. PATENT DOCUMENTS

| | | | | |
|---|---|---|---|---|
| 5,043,155 | A * | 8/1991 | Puchalski | ................ A61K 8/06 510/159 |
| 5,616,331 | A * | 4/1997 | Allard | .................. A61K 8/0204 424/401 |
| 5,658,575 | A * | 8/1997 | Ribier | .................. A61K 8/0295 424/401 |
| 6,288,121 | B1 | 9/2001 | Bader et al. | |
| 7,807,708 | B2 * | 10/2010 | Biadatti | ................ C07C 229/52 514/428 |
| 2011/0135584 | A1 | 6/2011 | Mallard | |

FOREIGN PATENT DOCUMENTS

| | | |
|---|---|---|
| EP | 0641557 A1 | 3/1995 |
| EP | 0973484 A1 | 1/2000 |
| WO | 2005/079730 A1 | 9/2005 |

OTHER PUBLICATIONS

English Translation of International Search Report dated Jul. 30, 2013 corresponding to International Patent Application No. PCT/EP2013/061192, 3 pages.

* cited by examiner

*Primary Examiner* — Mina Haghighatian
*Assistant Examiner* — Nathan W Schlientz
(74) *Attorney, Agent, or Firm* — Foley & Lardner LLP; Sunit Talapatra

(57) ABSTRACT

A method is described for producing an oil-in-water emulsion including oil globules, the mean diameter of which is less than 500 nm and each of which is provided with a lamellar liquid crystal coating, and which are dispersed in an aqueous phase. Each oil globule is individually coated with a unilamellar or oligolamellar layer obtained from at least one lipophilic surfactant, at least one hydrophilic surfactant, and at least one separate anionic surfactant, characterized in that the number of steps in the method is no greater than 5, in that the temperatures used during the different steps are no higher than 75° C., and in that the method requires neither the use of a high-pressure homogenizer nor any pre-emulsification step.

23 Claims, No Drawings

PROCESS FOR PREPARING A DERMATOLOGICAL COMPOSITION COMPRISING OLEOSOMES

CROSS-REFERENCE TO PRIOR APPLICATIONS

This application is a National Stage of PCT/EP2013/061192, filed May 30, 2013, and designating the United States (published Dec. 5, 2013, as WO 2013/178752 A1), which claims priority under 35 U.S.C. § 119 to U.S. Provisional Application No. 61/654,680, filed Jun. 1, 2012, and French Patent Application No. 1255107, filed Jun. 1, 2012, each hereby expressly incorporated by reference in its entirety and each assigned to the assignee hereof.

The present invention relates to a process for manufacturing a pharmaceutical composition, especially a dermatological composition, comprising oleosomes dispersed in an aqueous phase.

Compositions of oil-in-water emulsion type comprising coated liquid globules, also known as oleosomes, are known especially from patent EP 0 641 557. These compositions are oil-in-water emulsions formed from coated liquid globules (oleosomes), each provided with a lamellar liquid crystal coating and dispersed in an aqueous phase.

These oleosomes allow both the encapsulation of a lipophilic active principle in the liquid globules, and the dissolution or dispersion of the active principle in the outer aqueous phase.

The process for obtaining these systems described in the prior art is particular and involves:
 heating the two phases (fatty and aqueous) to a temperature of 80 to 95° C.;
 pre-emulsifying the two heated phases using a homogenizer for 30 minutes;
 treating several times successively in a high-pressure homogenizer (HPH) at 500 bar;
 cooling the emulsion for about 60 minutes; and finally
 adding the final aqueous phase (for example a gel) and stirring using a turbomixer equipped with a defloculating paddle.

Now, such a particular process for obtaining these systems has many drawbacks:
 it is complex, long, involves numerous steps (heating, pre-emulsification, several successive HPH treatments, cooling, gelation, which makes an average of seven steps) and uses different equipment for each;
 it requires particular equipment, i.e. the high-pressure homogenizer (HPH) for formation of the oleosomes at the time of emulsification;
 the heating temperatures are high (80 to 95° C.) before the mixing of the two phases, which excludes the incorporation of heat-sensitive excipients and active agents.

Furthermore, the successive treatments of the mixture in the HPH under pressure lead to an additional increase in the temperature of the mixture, which it is not possible to control; the process may thus lead to degradation of any heat-sensitive active principle(s) that may be introduced into the composition. This therefore constitutes a limiting factor with respect to the active principles and excipients that may be used.

There is thus a need for a process for manufacturing oleosomes that is simple to perform and readily industrializable, and which uses conventional production equipment.

The problem that the present invention proposes to solve here is thus that of designing a process for manufacturing a stable composition comprising oleosomes, which is simple, readily industrializable, which uses conventional equipment, which uses temperatures below 75° C. and which is thus suited to the incorporation of heat-sensitive excipients and/or active principles.

The Applicant has thus discovered, surprisingly, that a specific process, not using HPH, allows the production of stable oleosomes.

One subject of the present invention is thus a process for manufacturing an emulsion of oil-in-water type formed from liquid globules each bearing a lamellar liquid crystal coating and being dispersed in an aqueous phase, each oil globule being individually coated with a monolamellar or oligolamellar layer obtained from at least one lipophilic surfactant, at least one hydrophilic surfactant and at least one distinct anionic surfactant, comprising the following steps:
 a) mixing, at a temperature not above 75° C., preferably between 65° C. and 75° C., the lipophilic surfactant, the hydrophilic surfactant, the distinct anionic surfactant and all the ingredients of the liquid globules, so as to obtain a homogeneous mixture of fatty phase (A),
 b) mixing, at a temperature not above 75° C., preferably between 65° C. and 75° C., all the ingredients of the aqueous phase, so as to obtain a homogeneous mixture of aqueous phase (B),
 c) pouring the aqueous phase (B) obtained in b) into the fatty phase (A) obtained in a) with vigorous stirring, so as to obtain a homogeneous emulsion,
 d) cooling the homogeneous emulsion obtained in c), with slow stirring, until the temperature of the emulsion is less than or equal to 50° C.,
 said process comprising a number of steps less than or equal to 5.

The process does not require the use of a high-pressure homogenizer, does not involve a pre-emulsification step and every step of said process is performed at a temperature of less than or equal to 75° C.

As detailed in the examples, the process according to the invention is readily industrializable. Specifically, various batch sizes were produced (laboratory, pilot and industrial), which demonstrates that the process according to the invention is not only robust, but also reproducible and transposable to the various types of conventional equipment usually used, such as a rotor-stator stirrer, a turbomixer, a defloculating paddle and a planetary mixer (scrapers).

Preferably, the mixing step a) takes place at a temperature of between 65° C. and 75° C. and the mixing step b) takes place at a temperature of between 65° C. and 75° C.

The process according to the invention thus has the following advantages:
 it requires few manufacturing steps, about four steps. It is therefore faster and easier to perform than the processes of the prior art, especially during industrial production;
 it does not require a pre-emulsification step;
 it does not require special equipment that is difficult to transpose to the industrial scale. The manufacture of different batch sizes is performed by means of using conventional equipment conventionally used in the pharmaceutical or cosmetic industry;
 the heating temperatures before emulsification of the two phases are not more than 70° C. to 75° C. This temperature thus allows the incorporation into the composition of heat-sensitive excipients and/or active principles;
 it does not entail any substantial increase in temperature during the emulsification. It thus allows better control of the temperature and thus limits the risk of uncontrolled heating of the composition during the manufacture, thereby improving the stability of the composition;

finally, it allows the production of oleosomes with a mean diameter of less than 800 nm, without requiring the use of special equipment such as an HPH, or the use of high shears under pressure, which thus limits the risks of destabilization or of degradation of the composition.

Typically, the process according to the invention thus has the following characteristics:

it has a number of steps of less than or equal to 5,
it uses mixing temperatures not above 75° C.,
it does not require a pre-emulsification step,
it does not require the use of a high-pressure homogenizer. Thus, preferably, it does not comprise any high-pressure homogenization step.

Thus, the process according to the invention limits the risks of destabilization or degradation of the composition, i.e. it allows the production of a composition that is physically and chemically stable for 3 months at room temperature. According to a particular embodiment, the invention is directed toward the use of the process for manufacturing a composition comprising at least one heat-sensitive excipient and/or active principle, i.e. an excipient or active principle which degrades at temperatures above 75° C.

In addition, the process according to the invention makes it possible to obtain compositions for which the ratio between the aqueous phase and the fatty phase (coated liquid globules) is as follows:

% fatty phase/(% fatty phase+% aqueous phase) between 0.40 and 0.55, preferably between 0.45 and 0.50, and preferably equal to 0.48.

Composition Obtained Via the Process According to the Invention

The composition obtained via the process according to the invention may be a pharmaceutical composition, especially a dermatological or cosmetic composition. It is an oil-in-water emulsion, formed from oleosomes dispersed in an aqueous phase.

The term "oleosomes" refers to liquid globules individually coated with a monolamellar or oligolamellar liquid crystal layer obtained from at least one lipophilic surfactant, at least one hydrophilic surfactant and at least one distinct anionic surfactant. These oleosomes are dispersed in the aqueous phase (continuous phase).

Oleosomes are to be distinguished from lipid nanospheres. Specifically, oleosomes are liquid globules coated with a non-polymeric envelope that is solid at room temperature (i.e. formed from at least one lipophilic surfactant, at least one hydrophilic surfactant and at least one distinct anionic surfactant), as opposed to lipid nanospheres, which are matrix particles, i.e. all of the mass of which is solid at room temperature.

The oleosomes (coated liquid globules) have a mean diameter of less than 800 nm, preferably less than 600 nm and more particularly less than 500 nm. The mean diameter of the oleosomes and the particle size distribution may be determined by DLS (dynamic light scattering) using a particle size analyzer such as a Nano ZS Zetasizer (Malvern Instruments), as explained in the examples.

The composition may also comprise at least one active principle, which may be either dissolved in the liquid globules or dissolved in the continuous aqueous phase, or dispersed in the composition. The term "oligolamellar layer" means a layer comprising from 2 to 5 lipid leaflets.

The composition obtained via the process according to the invention is physically and chemically stable.

According to the invention the term "physical stability" refers to a composition whose physical properties such as the organoleptic properties, pH and viscosity are stable over time and under various temperature conditions (for example 4° C., room temperature and 40° C.).

The term "room temperature" means a temperature between 15 and 25° C.

According to the invention, the term "chemical stability" refers to a composition in which the pharmaceutical or cosmetic active agent is chemically stable over time, irrespective of the temperature condition: 4° C., room temperature, 40° C.

Preferably, the lipophilic surfactant used for forming the oleosomes has an HLB of between 2 and 5.

As lipophilic surfactant with an HLB of between 2 and 5 that may be used according to the invention, mention will be made of sorbitan esters, such as sorbitan monostearate (HLB=4.7) sold under the name Span® 60 by the company Croda, glycerol esters such as the glyceryl monostearate sold under the name Kolliwax® GMS II (HLB=3.8) by the company BASF, low-HLB sugar esters such as the sucrose dilaurate sold under the name Surfhope® C-1205 (HLB=5) or the sucrose tristearate sold under the name Surfhope® C-1803 (HLB=3) by the company Gattefossé, or alternatively polyoxyethylene stearyl ether comprising 2 oxyethylene units (2 OE).

Preferably, the lipophilic surfactant with an HLB of between 2 and 5 is chosen from sucrose distearate, sucrose tristearate, diglyceryl distearate, tetraglyceryl tristearate, decaglyceryl decastearate, diglyceryl monostearate, sorbitan monostearate, sorbitan tristearate, 15 diethylene glycol monostearate, the glyceryl ester of palmitic and stearic acids, polyoxyethylene monostearate comprising 2 oxyethylene units (2 OE), polyoxyethylene stearyl ether comprising 2 oxyethylene units (2 OE), glyceryl monobehenate and dibehenate and pentaerythrityl tetrastearate.

Preferably, the hydrophilic surfactant used for forming the oleosomes has an HLB of between 8 and 12.

Nonlimiting examples of hydrophilic surfactants with an HLB of between 8 and 12 that may be mentioned include polyoxyethylene glycol esters such as glyceryl stearate and PEG-100 stearate sold under the name Arlacel® 165 FL (HLB=11) by the company Croda, PEG-6 stearate and PEG-32 stearate sold under the name Tefose® 1500 (HLB=10) by the company Gattefossé, polyoxyethylene sorbitan esters and high-HLB sugar esters such as the sucrose stearate sold under the name Surfhope® C-1811 (HLB=11) by the company Gattefossé, or alternatively polyoxyethylene stearyl ether comprising 10 oxyethylene units. Preferably, the hydrophilic surfactant with an HLB of between 8 and 12 is chosen from polyoxyethylene (4) sorbitan monostearate (POE-4 sorbitan monostearate or polysorbate-61), polyoxyethylene (20) sorbitan tristearate, polyoxyethylene (8) monostearate, hexaglyceryl monostearate, polyoxyethylene (10) monostearate, polyoxyethylene (10) stearyl ether, polyoxyethylene (12) distearate and polyoxyethylene (20) methylglucose distearate.

The term "distinct anionic surfactant" means an anionic surfactant other than the lipophilic surfactant and the hydrophilic surfactant forming the coating of the oleosomes.

Preferably, the distinct anionic surfactant is a fatty acid or a fatty acid ester, said fatty acid comprising at least one saturated fatty chain containing more than 12 and preferably between 16 and 22 carbon atoms.

The distinct anionic surfactant may also be an ionic amphiphilic lipid. The ionic amphiphilic lipid is preferably chosen from the group comprising neutralized anionic lipids, amphoteric lipids and alkylsulfonic derivatives.

The neutralized anionic lipids are chosen in particular from:
- alkali metal salts of dicetyl phosphate, and in particular the sodium and potassium salts;
- alkali metal salts of dimyristyl phosphate, and in particular the sodium and potassium salts;
- alkali metal salts of cholesteryl sulfate, and in particular the sodium salt;
- alkali metal salts of cholesteryl phosphate, and in particular the sodium salt;
- monosodium and disodium salts of acylglutamic acids, and in particular the monosodium and disodium salts of N-stearoylglutamic acid, the sodium salt of phosphatidic acid.

The amphoteric lipids are chosen in particular from phospholipids and especially pure soybean phosphatidylethanolamine.

The alkylsulfonic derivatives are advantageously the compounds of formula:

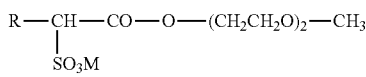

in which R represents the radicals $C_{16}H_{33}$ and $C_{18}H_{37}$ taken alone or as a mixture and M is an alkali metal, preferably sodium.

More preferentially, the distinct anionic surfactant is chosen from stearic acid, palmitic acid, arachidic acid and behenic acid. It may also be sodium stearoyl glutamate, sold under the name Eumulgin® SG by BASF or Amisoft® HS 11 by Ajinomoto.

Preferably, the surfactants are mixed in the following proportions to form the oleosomes:
- lipophilic surfactant (HLB between 2 and 5): 45-50% by weight of the mixture;
- hydrophilic surfactant (HLB between 8 and 12): 30-35% by weight of the mixture; and
- distinct anionic surfactant: 20-25% by weight of the mixture.

Preferably, the total amount of surfactants present in a composition obtained via the process according to the invention is between 3% and 4% of the total weight of the composition.

The liquid globules are typically composed of at least one oily excipient chosen from tocopherol esters, polyethoxylated fatty acids, triglycerides and oils containing the same, and fatty acid esters. They may also comprise one or more fatty substances that are liquid or semiliquid at room temperature. These compounds are especially mineral oils, plant oils, animal oils or silicone oils.

The term "oily phase" or "oily excipient" means any water-immiscible material of natural, animal or synthetic origin.

Among the triglycerides and oils containing the same, mention may be made in a nonlimiting manner of octanoic acid triglycerides or caprylic/capric acid triglycerides, such as those sold by the company Stéarineries Dubois or those sold under the names Miglyol® 810, 812 and 818 by the company Sasol.

Among the fatty acid esters, mention may be made in a nonlimiting manner of diisopropyl adipate and cetostearyl isononanoate.

As examples of mineral oils, mention may be made, for example, of liquid paraffins of various viscosities, such as Primol 352®, Marcol 52® and Marcol 152® sold by the company Esso.

As plant oils, mention may be made of sweet almond oil, coconut oil, palm oil, soybean oil, sesame oil and sunflower oil.

As animal oils, mention may be made of lanolin, squalene, fish oil, mink oil, with, as a derivative, the squalane sold under the name Cosbiol® by the company Laserson.

As volatile or nonvolatile silicone oils, mention may be made of dimethicones, for instance the product sold under the name Q7-9120® Silicone Fluid with a viscosity of 20 cSt to 12 500 cSt, or the product sold under the name ST-Cyclomethicone-5 NF® by the company Dow Corning.

Preferably, the composition according to the invention has a ratio between the total amount of surfactants and the total amount of oily phase constituting the liquid globules of between 10% and 25%. With such a ratio, the oleosomes have an acceptable size, with a lamellar liquid crystal coating around the droplets of monolamellar or oligolamellar oil.

The oleosomes are dispersed in an aqueous phase, which is the continuous phase.

The continuous aqueous phase comprises water. This water may be demineralized water, a floral water such as cornflower water, or a natural spring water or mineral water, chosen, for example, from Vittel water, Vichy basin water, Uriage water, Roche Posay water, Bourboule water, Enghien-les-Bains water, Saint Gervais-les-Bains water, Néris-les-Bains water, Allevard-les-Bains water, Digne water, Maizières water, Neyrac-les-Bains water, Lons-le-Saunier water, Eaux Bonnes water, Rochefort water, Saint Christau water, Fumades water, Tercis-les-Bains water, Avène water or Aix-les-Bains water.

The water may be present in a content of between 25% and 90% by weight and preferably between 50% and 90% by weight relative to the total weight of the composition.

The aqueous phase may also comprise humectants, preferentially polyols selected from glycerol, propylene glycol, dipropylene glycol, pentylene glycol, diglycerol and sorbitol.

The aqueous phase may also comprise a basic agent in dissolved form. This basic agent allows neutralization of the fatty acid present in the oleosomes as distinct anionic surfactant. This basic agent may be triethanolamine, sodium hydroxide, lysine or arginine.

The aqueous phase may also optionally comprise preserving agents, used alone or in combination, in order to effectively protect the formulations against any bacterial contamination. These preserving agents preferentially used in the invention are benzoic acid and potassium sorbate. They may be used in a content of from 0.01% to 5% and preferentially from 0.01% to 2%.

The aqueous phase may also optionally comprise additives, among which mention may be made of the following categories, alone or in combination: chelating agents, antioxidants, calmatives and/or anti-irritants, or any other additive usually used in the pharmaceutical or cosmetic field for giving said preparation specific properties.

The composition obtained via the process of the invention may comprise at least one pharmaceutical or cosmetic active agent. This active principle may be chosen from retinoids, glycyrrhetinic acid and zinc gluconate, alone or as a mixture.

Even more preferentially, the active principle is chosen from retinoids.

The retinoids that may be used in the context of the invention especially comprise all-trans-retinoic acid or tretinoin, 13-cis-retinoic acid or isotretinoin, acitretin, arotinoic acid, retinol, adapalene, tazarotene, retinaldehyde, etretinate and the compounds protected in patent application WO 2006/066 978 such as 3"-tert-butyl-4'-(2-hydroxyethoxy)-4"-pyrrolidin-1-yl-[1,1';3',1"]-terphenyl-4-carboxylic acid, the compounds of patent application FR 05/12367 including 2-hydroxy-4-[3-hydroxy-3-(5,6,7,8-tetrahydro-5,5,8,8-tetramethyl-2-naphthyl)-1-propynyl]benzoic acid or an enantiomer thereof, the compounds of patent application WO 05/56516 including 4'-(4-isopropylaminobutoxy)-3'-(5,5,8,8-tetramethyl-5,6,7,8-tetrahydronaphthalen-2-yl)-biphenyl-4-carboxylic acid, the compounds of patent application PCT/EP04/014809 including 4-{3-hydroxy-3-[4-(2-ethoxyethoxy)-5,5,8,8-tetramethyl-5,6,7,8-tetrahydronaphthalen-2-yl]-prop-1-ynyl}benzoic acid, and the compounds of patent application FR 2 861 069 including 4-[2-(3-tert-butyl-4-diethylaminophenyl)-2-hydroxyiminoethoxy]-2-hydroxybenzoic acid. 3"-tert-Butyl-4'-(2-hydroxyethoxy)-4"-pyrrolidin-1-yl-[1,1';3',1"]-terphenyl-4-carboxylic acid, as protected in patent application WO 2006/066 978, is particularly preferred.

In the case where the active principle is of retinoid type, the active principle may be present in an amount of between 0.00001% and 0.3% by weight relative to the total weight of the composition, preferably from 0.0001% to 0.1% and preferentially from 0.001% to 0.05% by weight relative to the total weight of the composition. In a preferred embodiment, the composition obtained according to the process of the invention comprises between 0.001% and 0.05% and more particularly between 0.003% and 0.03% by weight of 3"-tert-butyl-4'-(2-hydroxyethoxy)-4"-pyrrolidin-1-yl-[1,1';3',1"]-terphenyl-4-carboxylic acid relative to the total weight of the composition.

In another embodiment according to the invention, a person skilled in the art will define the concentration ranges as a function of the nature of the active agents and will adapt them, according to his knowledge, to the preferred use of the composition according to the invention.

The composition obtained via the process according to the invention may be incorporated into a pharmaceutically or cosmetically acceptable vehicle, such as a gel, a solution or an emulsion, for instance a cream or a sprayable or non-sprayable lotion.

When the pharmaceutically or cosmetically acceptable vehicle is a gel, the composition according to the invention is dispersed in a hydrophilic phase which comprises at least one gelling agent. This gelling agent may be a cellulose derivative chosen from semi-synthetic cellulose-based gelling agents, such as methylcellulose, ethylcellulose or hydroxypropylmethylcellulose sold by the company Colorcon under the name Methocel® (for example: Methocel® E4M), hydroxyethylcellulose sold by the company Ashland under the name Natrosol® (for example: Natrosol® 250 HHX), carboxymethylcellulose, hydroxymethylcellulose and hydroxypropylcellulose, taken alone or as a mixture. The gelling agent may also be chosen from natural gums such as gum tragacanth, guar gum, acacia gum, gum arabic, xanthan gum, starch and derivatives thereof, copolymers of polyacrylic acid, for instance the carbomer products sold by the company Lubrizol (i.e. Carbomer® 980), and of methyl methacrylate, carboxyvinyl polymers, polyvinylpyrrolidones and derivatives thereof, polyvinyl alcohols, biopolymers such as sodium alginate, pectin, dextrin, chitosan or sodium hyaluronate and derivatives thereof, taken alone or as a mixture. The gelling agent may also be chosen from the compound Sepigel® 305 consisting of a polyacrylamide/C13-C14 isoparaffin/laureth-7 mixture, or Simulgel® 600PHA or Sepineo® P600, namely sodium acryloyldimethyltaurate copolymer/isohexadecane/polysorbate 80, these two products being sold by the company SEPPIC.

The gelling agent is especially used in a concentration of between 0.1% and 10% by weight and preferably between 0.1% and 4% by weight relative to the total weight of the composition.

When the pharmaceutically or cosmetically acceptable vehicle is a solution, the composition according to the invention is dispersed in a vehicle composed of an aqueous phase (as defined previously in the present invention).

When the pharmaceutically or cosmetically acceptable vehicle is a cream or a lotion, the composition according to the invention is dispersed in a vehicle composed of an aqueous phase and of a fatty phase optionally comprising at least one surfactant or emulsifier.

The composition according to the invention may also contain additives or combinations of additives, such as:
co-surfactants such as fatty alcohols;
preserving agents;
pro-penetrants;
stabilizers;
humectants;
humidity regulators;
pH regulators;
osmotic pressure modifiers;
chelating agents;
UV-A and UV-B screening agents;
and antioxidants.

Needless to say, a person skilled in the art will take care to select the optional compound(s) to be added to these compositions such that the advantageous properties intrinsically associated with the present invention are not, or are not substantially, adversely affected by the envisaged addition. These additives may be present in the composition from 0 to 40% by weight relative to the total weight of the composition.

When the composition obtained according to the process of the invention comprises a pharmaceutical active agent, the composition may be used as a medicament.

In particular, when the composition obtained according to the process of the invention contains a retinoid, it may be used for treating dermatological complaints, especially human complaints, in particular acne, psoriasis, atopic dermatitis or palmoplantar keratosis.

When the composition obtained according to the process of the invention does not comprise a pharmaceutical active principle, or comprises a cosmetic active agent, the composition may be used in cosmetics in the field of caring for the skin, the integuments, the body or the hair. The composition especially has an advantage in the field of sun protection. Specifically, it has been noted that compositions containing oleosomes have improved sun protection factors when compared with compositions not containing these oleosomes. The compositions obtained according to the process of the invention also have this advantage.

Processes According to the Invention

As indicated above, one subject of the present invention is a process for manufacturing an emulsion of oil-in-water type formed from liquid globules each bearing a lamellar liquid crystal coating and being dispersed in an aqueous phase, each oil globule being individually coated with a monolamellar or oligolamellar layer obtained from at least one lipophilic surfactant, at least one hydrophilic surfactant and at least one distinct anionic surfactant, comprising the following steps:
- a) mixing, at a temperature not above 75° C., preferably between 65° C. and 75° C., the lipophilic surfactant, the hydrophilic surfactant, the distinct anionic surfactant and all the ingredients of the liquid globules, so as to obtain a homogeneous mixture of fatty phase (A),
- b) mixing, at a temperature not above 75° C., preferably between 65° C. and 75° C., all the ingredients of the aqueous phase, so as to obtain a homogeneous mixture of aqueous phase (B),
- c) pouring the aqueous phase (B) obtained in b) into the fatty phase (A) obtained in a) with vigorous stirring, so as to obtain a homogeneous emulsion,
- d) cooling the homogeneous emulsion obtained in c), with slow stirring, until the temperature of the emulsion is less than or equal to 50° C.

This process is simple and does not use a high-pressure homogenizer (HPH).

Moreover, the process according to the invention does not require a pre-emulsification step and every step of said process is performed at a temperature of less than or equal to 75° C.

The term "vigorous stirring" means stirring performed:
- using a homogenizer of rotor/stator type whose stirring speed is greater than 5000 rpm and preferentially greater than 10 000 rpm;
- using a turbomixer whose stirring speed is greater than 700 rpm, preferentially greater than 1000 rpm and more preferentially greater than 2000 rpm.

The mixing in steps a) and b) may be concomitant or successive.

Preferably, the mixing in step a) is performed using a turbomixer, preferably at a speed of between 700 rpm and 1500 rpm, and optionally with a coaxial speed of between 20 rpm and 40 rpm. Preferably, this mixing is performed at a temperature of about 70° C. After this step a), the fatty phase (A) is obtained.

Preferably, the mixing in step b) is performed using a turbomixer, preferably at a speed of between 150 rpm and 1500 rpm. Preferably, this mixing is performed at a temperature of about 70° C. After this step b), the aqueous phase (B) is obtained. This aqueous phase comprises water, and optionally hydrophilic compounds, especially a basic agent.

In steps a) and b), the mixing is performed with stirring until the fatty phase (A) and aqueous phase (B) are homogeneous.

Next, the aqueous phase (B) is poured into the fatty phase (A) with vigorous stirring (step c)): this is the emulsification step.

When the batch is manufactured at the laboratory scale, the aqueous phase (B) is poured into the fatty phase (A) using a rotor-stator stirrer at a speed of between 10 000 rpm and 13 000 rpm, for a time of between 25 minutes and 1 hour. Preferably, the emulsification in step c) takes place for a time of between 30 and 40 minutes.

When the batch is manufactured at the pilot or industrial scale, the emulsification is performed by sucking the aqueous phase (B) into the fatty phase (A), at a coaxial speed of between 45 rpm and 100 rpm, and with stirring at a speed of between 1000 rpm and 3000 rpm. For example, the emulsification may be performed by sucking the aqueous phase (B) into the fatty phase (A) with a pipe, at a coaxial speed of between 45 rpm and 100 rpm, and with stirring at a speed of between 1000 rpm and 3000 rpm, and optionally with a scraping speed of about 25 rpm.

In step c), typically, the stirring is continued until a liquid which has, under an optical microscope, a very fine emulsion carpet is obtained.

Next, the mixture obtained in step c) is cooled: this is the cooling step d). Typically, the cooling in step d) is performed by introducing water into the mixture obtained in c), with stirring at a speed of between 1000 rpm and 3000 rpm, and at a coaxial speed of between 40 rpm and 50 rpm, until the temperature of the emulsion is less than or equal to 50° C. Preferably, the cooling in step d) is performed by introducing water into the mixture obtained in c), with stirring at a speed of between 1000 rpm and 3000 rpm, and at a coaxial speed of between 40 rpm and 50 rpm, until the temperature of the emulsion is less than or equal to 40° C.

At the end of step d), an emulsion comprising the oleosomes is obtained.

This emulsion may be used as obtained, or may be gelled. In the latter case, a gelling agent may be introduced into the cooled mixture obtained in d), with stirring at a speed of between 1000 rpm and 2000 rpm, until a cream is obtained.

When the emulsion comprises an active principle, this active principle may be introduced into the fatty phase during step a), or into the aqueous phase (B) during step b), or alternatively after the emulsification step c), or else after the cooling step d).

Various processes for manufacturing formulations according to the invention will now be given, as illustrations and with no limiting nature.

EXAMPLE 1

Manufacturing Process at the Laboratory Scale
(100 g-2 kg)

The composition that follows is prepared according to the protocol indicated below.

Its macroscopic and microscopic appearance at T0 are studied, and the pH is measured.

The viscosity is also measured using a Brookfield viscometer.

The physical and chemical stability are evaluated at 1, 2 and 3 months, at room temperature (RT) and at 40° C.

The size of the oleosomes was checked just after manufacture by DLS (dynamic light scattering) using a Nano ZS Zetasizer particle size analyzer (Malvern Instruments), after diluting the samples in distilled water.

The results obtained are given after each composition.

| | Trade name | INCI name | % |
|---|---|---|---|
| | — | 3"-tert-Butyl-4'-(2-hydroxyethoxy)-4"-pyrrolidin-1-yl-[1,1'; 3',1"]-terphenyl-4-carboxylic acid ("active agent" hereinbelow) | 0.01 |
| A | BRIJ S10-SO | STEARETH-10 | 1.25 |

EXAMPLE 1 - Composition

| | | | |
|---|---|---|---|
| A | SPEZIOL L2SM GS PHARMA | STEARIC-/PALMITIC ACID | 0.85 |
| A | BRIJ S2-SO | STEARETH-2 | 1.80 |
| A | SPEZIOL C18 PHARMA | STEARYL ALCOHOL | 0.25 |
| A | MIGLYOL 812 N | CAPRYLIC/CAPRIC TRIGLYCERIDES | 15.50 |
| A | PHENOXETOL | PHENOXYETHANOL | 1.00 |
| A | DL-ALPHA-TOCOPHEROL | ALPHA TOCOPHEROL | 0.20 |
| A | ST-CYCLOMETHICONE 5-NF | CYCLOPENTASILOXANE | 4.00 |
| B | PURIFIED WATER | AQUA (WATER) | 21.80 |
| B | TRIETHANOLAMINE | TRIETHANOLAMINE | 0.20 |
| B | TITRIPLEX III | DISODIUM EDETATE | 0.10 |
| B | GLYCEROL | GLYCEROL | 5.00 |
| B | NIPAGIN M | METHYL PARABEN | 0.20 |
| C | PURIFIED WATER | AQUA (WATER) | 43.84 |
| D | SIMULGEL 600 PHA | ACRYLAMIDE/SODIUM ACRYLOYLDIMETHYL TAURATE COPOLYMER & ISOHEXADECANE & POLYSORBATE 80 | 4.00 |

| CHARACTERIZATION At T0 | MACROSCOPIC APPEARANCE | Thick, white, glossy cream |
|---|---|---|
| | MICROSCOPIC APPEARANCE | Fine, homogeneous emulsion carpet |
| | pH | 7.53 |
| | VISCOSITY | 830000 cp |
| | | 92.8% |
| | MEAN DIAMETER | 377 nm |

| Monitoring of stabilities | | | 1 MONTH | 2 MONTHS | 3 MONTHS |
|---|---|---|---|---|---|
| Physical stability | pH RT/40° C. | | 7.45/7.37 | 7.38/7.29 | 7.42/7.27 |
| | Viscosity | RT | 827000 cP | 831000 cP | 826500 cP |
| | | | 91.4% | 89.8% | 83.2% |
| | | 40° C. | 826000 cP | 821000 cP | 823000 cP |
| | | | 88.9% | 78.6% | 77.2% |
| Chemical stability | Assay (% relative | RT | 101.4% | 100.5% | 100.0% |
| | active agent/T0) | 40° C. | 101.2% | 97.1% | 99.1% |

Equipment Used:

Formulation beakers of suitable size

Rotor-stator stirrer: Polytron®

Stirrer equipped with a deflocculating paddle: VMI-Rayneri Turbotest

Preparation of the Two Phases

Weigh out all the elements of the fatty phase (A) in a formulation beaker and heat them at 70° C., with magnetic stirring, until a homogeneous mixture is obtained.

Weigh out all the elements of the aqueous phase (B) in an additional beaker and heat them at 70° C., with magnetic stirring, until a clear mixture is obtained.

Emulsification

Pour the aqueous phase (B) rapidly into the fatty phase (A) with vigorous stirring: Rotor-stator: 10000-13000 rpm.

Keep stirring for 30-40 minutes, until a fine fluid emulsion is obtained.

Cooling

Stop the Polytron® stirring and place the beaker containing the emulsion in a cold-water bath to promote rapid cooling.

Next, stir the emulsion slowly (deflocculating paddle-200 rpm).

Gradually add the cooling water (phase C).

Keep stirring slowly until the temperature of the emulsion is below 25° C.

Gelation

Gradually add the gelling agent (phase D) to the emulsion with moderate to vigorous stirring:

Rayneri blender with a deflocculating paddle: 500-800 rpm.

Keep stirring until a glossy smooth cream is obtained

EXAMPLE 2

Manufacturing Process at the Pilot Scale (10 kg)

The composition that follows is prepared according to the protocol indicated below. The macroscopic and microscopic appearance at T0 are studied.

The results obtained are given after each composition.

| EXAMPLE 2 - Composition | | | |
|---|---|---|---|
| Phase | Trade name | INCI name | (w/w %) |
| A1 | BRIJ S10-SO | STEARETH-10 | 1.25 |
| A1 | KOLLIWAX S | STEARIC-/PALMITIC ACID | 0.85 |
| A1 | BRIJ S2-SO | STEARETH-2 | 1.80 |
| A1 | KOLLIWAX SA | STEARYL ALCOHOL | 0.25 |
| A1 | MIGLYOL 812 N | CAPRYLIC/CAPRIC TRIGLYCERIDES | 11.50 |
| A1 | ST-CYCLOMETHICONE 5-NF | CYCLO-PENTASILOXANE | 4.00 |
| A2 | PHENOXETOL | PHENOXYETHANOL | 1.00 |
| A2 | MIGLYOL 812 N | CAPRYLIC/CAPRIC TRIGLYCERIDES | 4.00 |
| A2 | DL-ALPHA-TOCOPHEROL | ALPHA TOCOPHEROL | 0.20 |
| B1 | PURIFIED WATER | AQUA (WATER) | 21.41 |
| B1 | GLYCEROL | GLYCEROL | 5.00 |
| B1 | BENZALKONIUM CHLORIDE | BENZALKONIUM CHLORIDE | 0.08 |
| B1 | TRIETHANOLAMINE | TRIETHANOLAMINE | 0.20 |
| B2 | PURIFIED WATER | AQUA (WATER) | 41.06 |
| B3 | BENZYL ALCOHOL | BENZYL ALCOHOL | 0.40 |
| B3 | PURIFIED WATER | AQUA (WATER) | 3.00 |
| C | SIMULGEL 600 PHA | ACRYLAMIDE/SODIUM ACRYLOYLDIMETHYL TAURATE COPOLYMER & ISOHEXADECANE | 4.00 |

-continued

| EXAMPLE 2 - Composition & POLYSORBATE 80 | | |
|---|---|---|
| CHARACTERIZA-<br>TION At T0 | MACROSCOPIC<br>APPEARENCE | Thick, white,<br>glossy cream |
| | MICROSCOPIC<br>APPEARENCE | Fine,<br>homogeneous<br>emulsion carpet |
| | MEAN DIAMETER | 440 nm |

Equipment Used:
  Aqueous phase: OLSA melting vat
  Fatty phase: OLSA tank (preparation tank)
Preparation of the Fatty Phase (Phases A1+A2)
  Place the various elements of the fatty phase A1 in an Olsa tank with stirring. Stir using a turbomixer at 1500 rpm.
  Switch off the turbomixer and heat the mixture to 70° C. with coaxial stirring (30 rpm).
  Add the rest of the fatty phase (A2) with coaxial stirring until a clear mixture is obtained.
Preparation of the Aqueous Phase (Phase B1)
  Place the various elements of the aqueous phase (phase B1) in an Olsa melting vat.
  Heat the mixture at 70° C. with stirring (150 rpm) while covering the melting vat to limit the evaporation, until all the excipients are fully dissolved and the mixture becomes clear.
Emulsification
  While stirring with a turbomixer, transfer the aqueous phase very slowly by suction from the bottom of the tank (Olsa melting vat) into the fatty phase (Olsa tank) using a pipe:
  Coaxial speed: 45 rpm
  Turbomixer speed: 3000 rpm
  Maintain the stirrings and the temperature (70° C.) until emulsification of the two phases is complete and a glossy, opaque, white liquid is obtained, which has, under an optical microscope, a very fine emulsion carpet.
Cooling
  Introduce into the Olsa tank with stirring, by suction from the bottom of the tank, the cooling water (phase B2):
  Coaxial speed: 45 rpm
  Turbomixer speed: 3000 rpm
  Cool the mixture to 40° C. with stirring:
  Coaxial speed: 45 rpm
  Turbomixer speed: 3000 rpm
  When the mixture is at 40° C., add phase B3 with continued stirring.
Gelation
  Introduce the gelling agent (phase C) into the preceding mixture at 40° C., with stirring:
  Coaxial speed: 45 rpm
  Turbomixer speed: 2000 rpm
  Cool to 25° C. with stirring, and keep stirring until a smooth, glossy white cream is obtained.

EXAMPLE 3

Manufacturing Process at the Industrial Scale (4000 kg)

The composition that follows is prepared according to the protocol indicated below.

| EXAMPLE 3 - Composition | | | |
|---|---|---|---|
| Phase | Trade name | Ingredients (INCI name) | Content % |
| A | NEO HELIOPAN OS/BP | ETHYLHEXYL SALICYLATE | 29.05 |
| | NEO HELIOPAN 303 | OCTOCRYLENE | |
| | PARSOL 1789 | BUTYLMETHOXY-DIBENZOYLMETHANE | |
| | SILICONS FLUID 200 350 cST | DIMETHICONE | |
| | TWEEN 61V | POLYSORBATE 61 | |
| | AMISOFT HS 11 | SODIUM STEARYL GLUCAMATE | |
| | RYOTO SUGAR ESTER S370 | SUCROSE TRISTEARATE | |
| | DUB DIS | DIISOPROPYLE SEBACATE | |
| | ELDEW SL 205 | ISOPROPYL LAURYL SARCOSINATE | |
| | ENOXOLONE/ PLANTACTIV GLA 18 | GLYCYRRHETINIC ACID | |
| B | CERAMIDE 5 | HYDROXYPALMITOYL SPHINGANINE AQUA (WATER) | 42.8 |
| | PURIFIED WATER | | |
| | RONACARE ALLANTOIN | ALLANTOIN | |
| | TITRIPLEX III | DISODIUM EDETATE | |
| | PHENOXETOL | PHENOXYETHANOL | |
| | HYDROLITE-5 | PENTYLENE GLYCOL | |
| | DERMOSOFT OCTIOL | CAPRYLYL GLYCOL | |
| | D-PANTHENOL USP | PANTHENOL | |
| | GLYCEROL 4810 | GLYCEROL | |
| C | DL ALPHA TOCOPHEROL ACETATE | TOCOPHERYL ACETATE | 19.95 |
| | PURIFIED WATER | AQUA (WATER) | |
| | — | POTASSIUM SORBATE | |
| | — | ZINC GLUCONATE | |
| | RHODICARE XT | XANTHAN GUM | |
| | CARBOPOL 980 | CARBOMER | |
| D | TRIETHANOLAMINE CARE | TRIETHANOLAMINE | 2.2 |
| | DC 1503 FLUID | DIMETHICONE (AND) DIMETHICONOL | |
| E | DRY FLO PLUS | ALUMINUM STARCH OCTENYLSUCCINATE | 6 |
| | SILICA BEAD SB 150 | SILICA | |
| | MICROPEARL M100 | POLYMETHYL METHACRYLATE | |

Equipment Used:
  #4000 L skid with melting vat (preparation tank)
  2 100 L containers, made of stainless steel
  1 200 L container, made of stainless steel
  2 20 kg containers, made of stainless steel
Preparation of the Fatty Phase (Phase A)
  Place the various elements of the fatty phase A in the main tank with stirring.
  Heat the mixture to 70° C. with stirring:
  Coaxial speed: 20-40 rpm
  Scrapers: 20 rpm
  Turbomixer speed: 700-1500 rpm
Preparation of the Aqueous Phase (Phase B)
  Place the various elements of the aqueous phase in a melting vat.
  Heat the mixture to 70° C. with stirring:
  Scrapers: 10-20 rpm
  Turbomixer speed: 1000-1500 rpm
  Keep stirring and heating until all the excipients are fully dissolved and the mixture becomes clear.
Emulsification
  While stirring with a turbomixer, transfer the aqueous phase by suction from the bottom of the tank (melting vat) into the fatty phase (main preparation tank) using a pipe:

Coaxial speed: 60-100 rpm
Scrapers: 25 rpm
Turbomixer speed: 1000-1800 rpm
Keep stirring until emulsification of the two phases is complete and a glossy, opaque, white liquid is obtained, which has, under an optical microscope, a very fine emulsion carpet.
Cooling
Cool the mixture in the main tank to 50° C. with stirring:
Coaxial speed: 50-100 rpm
Turbomixer speed: 1000-1800 rpm
Weigh out in a suitable container the elements of phase C, and stir until the excipients are homogeneously dispersed in the water:
Scrapers: 20-30 rpm
Turbomixer speed: 2000-3000 rpm
Introduce the cooling phase C into the preparation tank with stirring, by suction from the bottom of the tank:
Coaxial speed: 40 rpm
Scrapers: 20 rpm
Turbonnixer speed: 1000-1800 rpm
Gelation
When the preparation is at 40° C., introduce phase D into the preceding mixture with stirring:
Scrapers: 0-20 rpm
Turbomixer speed: 1000-1800 rpm
Add the elements of phase E.
Keep stirring until a glossy, smooth, white cream is obtained In Example 3, the content of phase A is 29.05% by weight, the content of phase B is 42.8% by weight, the content of phase C is 19.95% by weight, the content of phase D is 2.2% and the content of phase E is 6% by weight.

The invention claimed is:
1. A process of manufacturing an oil-in-water emulsion, the process comprising:
(a) mixing, at a temperature of between 65° C. and 75° C., at least one lipophilic surfactant, at least one hydrophilic surfactant, and at least one anionic surfactant to obtain a homogeneous fatty phase mixture (A), wherein the fatty phase mixture (A) comprises 45% to 50% by weight relative to the total weight of the fatty phase mixture (A) of the lipophilic surfactant, 30% to 35% by weight relative to the total weight of the fatty phase mixture (A) of the hydrophilic surfactant, and 20% to 25% by weight relative to the total weight of the fatty phase mixture (A) of the anionic surfactant,
(b) heating a homogeneous aqueous phase mixture (B) to a temperature of between 65° C. and 75° C.,
(c) stirring the homogenous aqueous phase mixture (B) of (b) into the fatty phase mixture (A) of (a) to obtain a homogeneous emulsion, wherein the stirring is performed with a homogenizer at a speed between 10,000 rpm and 13,000 rpm or a turbomixer at a speed between 700 rpm and 3000 rpm between 25 minutes to 1 hour, and
(d) cooling the homogeneous emulsion of (c) by introducing water into the mixture and stirring at a speed of between 1000 rpm and 3000 rpm until the temperature of the emulsion is between 25° C. and 50° C. to provide the oil-in-water emulsion,
wherein:
the oil-in-water emulsion comprises oil globules dispersed in the aqueous phase mixture (B) and each of the globules have a lamellar liquid crystal coating that is a monolamellar layer or an oligolamellar layer obtained from the lipophilic surfactant, the hydrophilic surfactant, and the anionic surfactant,
the homogeneous aqueous phase mixture (B) comprises water and optionally a humectant, a basic agent, preserving agent, chelating agent, antioxidant, calmatives, anti-irritants, or combinations of two or more thereof, and
every step of the process is performed at a temperature of less than or equal to 75° C., without a high pressure homogenizer, and without a pre-emulsification step, wherein the pre-emulsification consists of homogenizing the homogeneous fatty phase mixture (A) and the homogeneous aqueous phase mixture (B) in which both are heated to a temperature of 80° C. to 95° C.

2. The process as claimed in claim 1, wherein at least one lipophilic surfactant has an HLB of between 2 and 5.

3. The process as claimed in claim 2, wherein the lipophilic surfactant with an HLB of between 2 and 5 is selected from the group consisting of sucrose distearate, sucrose tristearate, diglyceryl distearate, tetraglyceryl tristearate, decaglyceryl decastearate, diglyceryl monostearate, sorbitan monostearate, sorbitan tristearate, 15 diethylene glycol monostearate, a glyceryl ester of palmitic acid, stearic acid, polyoxyethylene monostearate comprising 2 oxyethylene units, polyoxyethylene stearyl ether comprising 2 oxyethylene units, glyceryl monobehenate, glyceryl dibehenate and pentaerythrityl tetrastearate.

4. The process as claimed in claim 1, wherein at least one hydrophilic surfactant has an HLB of between 8 and 12.

5. The process as claimed in claim 4, wherein the hydrophilic surfactant with an HLB of between 8 and 12 is selected from the group consisting of polyoxyethylene sorbitan monostearate, polyoxyethylene sorbitan tristearate, polyoxyethylene monostearate, hexaglyceryl monostearate, polyoxyethylene (10) monostearate, polyoxyethylene stearyl ether, polyoxyethylene distearate, and polyoxyethylene methylglucose distearate.

6. The process as claimed in claim 1, wherein the distinct anionic surfactant is a fatty acid or a fatty acid ester, the fatty acid comprising at least one saturated fatty chain having more than 12 carbon atoms, neutralized anionic lipids, amphoteric lipids, and alkylsulfonic derivatives.

7. The process as claimed in claim 6, wherein the fatty acid comprising at least one saturated fatty chain has between 16 and 22 carbon atoms.

8. The process as claimed in claim 1, wherein the distinct anionic surfactant is selected from the group consisting of stearic acid, palmitic acid, arachidic acid, behenic acid, and sodium stearoyl glutamate.

9. The process as claimed in claim 1, wherein the oil-in-water emulsion further comprises at least one active agent selected from the group consisting of a retinoid, glycyrrhetinic acid, and zinc gluconate.

10. The process as claimed in claim 9, wherein the active agent is 3"-tert-butyl-4'-(2-hydroxyethoxy)-4"-pyrrolidin-1-yl-[1,1',3',1"]-terphenyl-4-carboxylic acid.

11. The process as claimed in claim 9, wherein the oil-in-water emulsion comprises a retinoid in an amount of from 0.00001% to 0.05% by weight relative to the total weight of the oil-in-water emulsion.

12. The process as claimed in claim 1, wherein the mixing step a) is conducted with vigorous stirring by a turbomixer.

13. The process as claimed in claim 12, wherein the turbomixer of step a) is operated at a speed of from 700 rpm to 1500 rpm.

14. The process as claimed in claim 13, wherein the turbomixer of step a) is operated at a coaxial speed of from 20 rpm to 40 rpm.

15. The process as claimed in claim 1, wherein the mixing step c) is conducted with vigorous stirring by a turbomixer.

16. The process as claimed in claim 15, wherein the turbomixer of step c) is operated at a coaxial speed of between 20 rpm and 40 rpm.

17. The process as claimed in claim 1, wherein the mixing in step c) is conducted with vigorous stirring by a rotor-stator stirrer.

18. The process as claimed in claim 1, wherein the cooling in step d) is performed by introducing water into the mixture obtained in step c) until the temperature of the emulsion is less than or equal to 40° C.

19. The process as claimed in claim 1, wherein a gelling agent is introduced into the cooled mixture obtained in step d) to obtain a cream.

20. The process as claimed in claim 1, wherein the process limits destabilization or degradation of the emulsion.

21. The process as claimed in claim 1 wherein at least one heat-sensitive excipient and/or active principle is introduced into the fatty phase mixture (A) during step a), into the aqueous phase mixture (B) during step b), into the emulsion after step c) and before step d), or after cooling step d).

22. The process as claimed in claim 1, wherein the homogeneous aqueous phase mixture (B) comprises between 25% and 90% by weight water.

23. The process as claimed in claim 1, wherein the globules have a mean diameter of less than 800 nm.

* * * * *